United States Patent [19]
Snyder et al.

[11] Patent Number: 5,437,795
[45] Date of Patent: Aug. 1, 1995

[54] CHROMATOGRAPHIC SEPARATION OF ERBIUM ISOTOPES

[75] Inventors: Thomas S. Snyder, Oakmont; Steven H. Peterson; Umesh P. Nayak, both of Murrysville; Richard J. Beleski, Pittsburgh, all of Pa.

[73] Assignee: Westinghouse Electric Corporation, Pittsburgh, Pa.

[21] Appl. No.: 264,810

[22] Filed: Jun. 23, 1994

[51] Int. Cl.⁶ ............................................. B01D 15/08
[52] U.S. Cl. .................... 210/635; 210/656; 210/657; 210/659; 210/198.2; 423/21.5; 423/263
[58] Field of Search ............... 210/635, 656, 657, 659, 210/198.2; 423/263, 21.1, 21.5

[56] References Cited

U.S. PATENT DOCUMENTS

| | | | |
|---|---|---|---|
| 3,582,263 | 6/1971 | Chiola et al. | 23/22 |
| 3,615,173 | 10/1971 | Winget | 423/21.5 |
| 4,394,353 | 7/1983 | Miyake et al. | 423/21.5 |
| 4,438,078 | 3/1984 | Nalewajek | 423/21.5 |
| 4,514,367 | 4/1985 | Asami et al. | 423/21.5 |
| 4,711,768 | 12/1987 | Peterson et al. | 423/21.5 |
| 4,915,843 | 4/1990 | Taniguchi | 210/635 |
| 5,024,749 | 6/1991 | Snyder | 210/198.2 |
| 5,045,209 | 9/1991 | Snyder et al. | 210/656 |
| 5,098,678 | 3/1992 | Lee et al. | 423/70 |
| 5,110,566 | 5/1992 | Snyder et al. | 423/70 |
| 5,124,023 | 6/1992 | Bosserman | 210/659 |
| 5,133,869 | 7/1992 | Taniguchi | 210/659 |
| 5,174,971 | 12/1992 | Snyder et al. | 423/70 |

*Primary Examiner*—Ernest G. Therkorn

[57] ABSTRACT

A process for the partial or complete simultaneous separation of isotopes of erbium, especially high thermal neutron capture cross-section erbium isotopes, using continuous, steady-state, chromatography in which an ion exchange resin is the stationary phase, an aqueous solution of ions based on a mixture of erbium isotopes is the feed phase, and an aqueous acid eluant solution is the mobile phase. The process involves the mobile phase eluting or desorbing the erbium isotopic solute adsorbed on the stationary phase under conditions such that each of the various naturally occurring isotopes of erbium is primarily eluted in an elution volume distinct from the elution volumes of the other isotopes. In a preferred embodiment, the conditions are such that at least one of the elution volumes contains essentially only one isotope of erbium. The process is preferably conducted in a continuous, steady-state manner, and in particular is preferably conducted in a continuous annular chromatograph (CAC).

13 Claims, 4 Drawing Sheets

CHROMATOGRAPHIC SEPARATION OF ERBIUM ISOTOPES

BACKGROUND OF THE INVENTION

1. Field of the Invention

The present invention is concerned with processing erbium to obtain a lower average thermal neutron capture cross section by a partial or complete separation of its isotopes thus improving its suitability as an internal material of construction, for instance, as a fuel rod cladding, for a nuclear reactor.

2. Background Information

The role of erbium (Er) in nuclear fuel assembly design is as a burnable poison with high neutron capture cross-section. Its properties are comparable or superior to Boron. Its chemical properties are similar to those of gadolinium (Gd) except that Er(III) is a slightly more acidic ion than Gd(III) in solution; therefore, its separation chemistry should be somewhat more powerful than that of Gd in a similar series of eluents.

The key issue in designing an enrichment system for the Er isotopic enrichment chemistry is that the key fractions of the high cross-section isotopes are embedded in undesirable isotopes. This results in the requirement of multiple extraction trains when using separations technologies such as solvent extraction or fixed bed ion exchange columns which generically produce only "heads" and "tails" fractions but nothing in the "middle". Hence, multiple trains are required to essentially dissect the fractions until the desired head or tail emerges from the column as the sole constituent of the product fraction. When combining this enrichment issue with the fact that Er separation from the ores requires both complex chemistry and hardware, one arrives at the summary of issues that must be addressed by a process technology that recovers Er from the raw ore and refines it to an isotopically pure product for inclusion in nuclear fuel assembly design:

a. Separation of erbium from the other rare-earth elements and impurities in the ore leachate
  1. requires a large number of multi-stage extraction circuits due to relatively low specificity of distribution coefficients for most extraction solvents;
  2. requires a large number of large, awkward, expensive stages per extraction circuit due to the low magnitude of the distribution coefficients;
  3. generates hazardous and mixed wastes as a result of the organic based solvents; and
  4. requires significant peripheral purification operations to refine the erbium once it is separated from the other rare-earths and to prepare it for isotopic enrichment.

b. Lack of a powerful, compact, cost-effective enrichment process which, again, generates no hazardous waste as a byproduct. Solvent extraction is ineffective due to the inherently low separation alpha's (driven by the fact that trivalent ions do not form readily separable solution complexes), and to its large, capital-intensive, separation stages that increase both operating and maintenance costs, generate hazardous process wastes (and possibly hazardous/radioactive mixtures depending on the composition of the original feed) and decrease process availability.

c. There is a lack of a mechanically-feasible continuous ion exchange contactor design to overcome the historical problems associated with ion exchange. These historical problems are:
  1. inherent batchwise operation;
  2. awkward valving required for product recovery when columns are operated in the chromatographic mode;
  3. complex process control problems associated with process operation and wave front separation; and
  4. excessive product dilution associated with column operation, and others.

OBJECTS OF THE INVENTION

It is, therefore, an object of the present invention to teach a separations art which overcomes these problems, which uses no hazardous organic solvents, and which consolidates purification and separation operations into a single operation.

It is also an object of the present invention to provide a process for isolating erbium 167 which has a low thermal neutron capture cross-section.

It is a further object of the present invention to provide a more efficient process than solvent extraction by utilizing a chromatographic technique.

It is yet another object of the present invention to provide a continuous technique for separating erbium 167 utilizing a continuously operating chromatographic technique.

SUMMARY OF THE INVENTION

A process for the partial or complete separation of the isotopes of erbium using chromatography has been developed in which a cation exchange resin is the stationary phase, an aqueous solution of an ionic compound of a mixture of erbium isotopes is the feed, and an aqueous acid solution is the mobile phase. The process involves the mobile phase eluting the erbium isotopic solute under conditions such that each of the various naturally occurring isotopes of erbium is primarily eluted in an elution volume distinct from the elution volumes of the other isotopes. In a preferred embodiment the conditions are such that at least one of the elution volumes contains essentially only one isotope of erbium. The process is preferably conducted in a steady state, continuous manner, and it is particularly preferred to conduct it in a continuous annular chromatograph.

A particular preferred embodiment involves feeding erbium oxide dissolved in an aqueous mineral acid to a continuous annular chromatograph with a stationary phase which comprises a cation exchange resin. The mobile phase for the elution is preferably aqueous hydrochloric acid, possibly with the addition of chelants, complexants, or ligands—particularly to the mobile phase chemistry—to enhance separation. However, sulfuric, nitric and specialized admixtures are all useable.

DETAILED DESCRIPTION OF THE INVENTION

Figure 1:
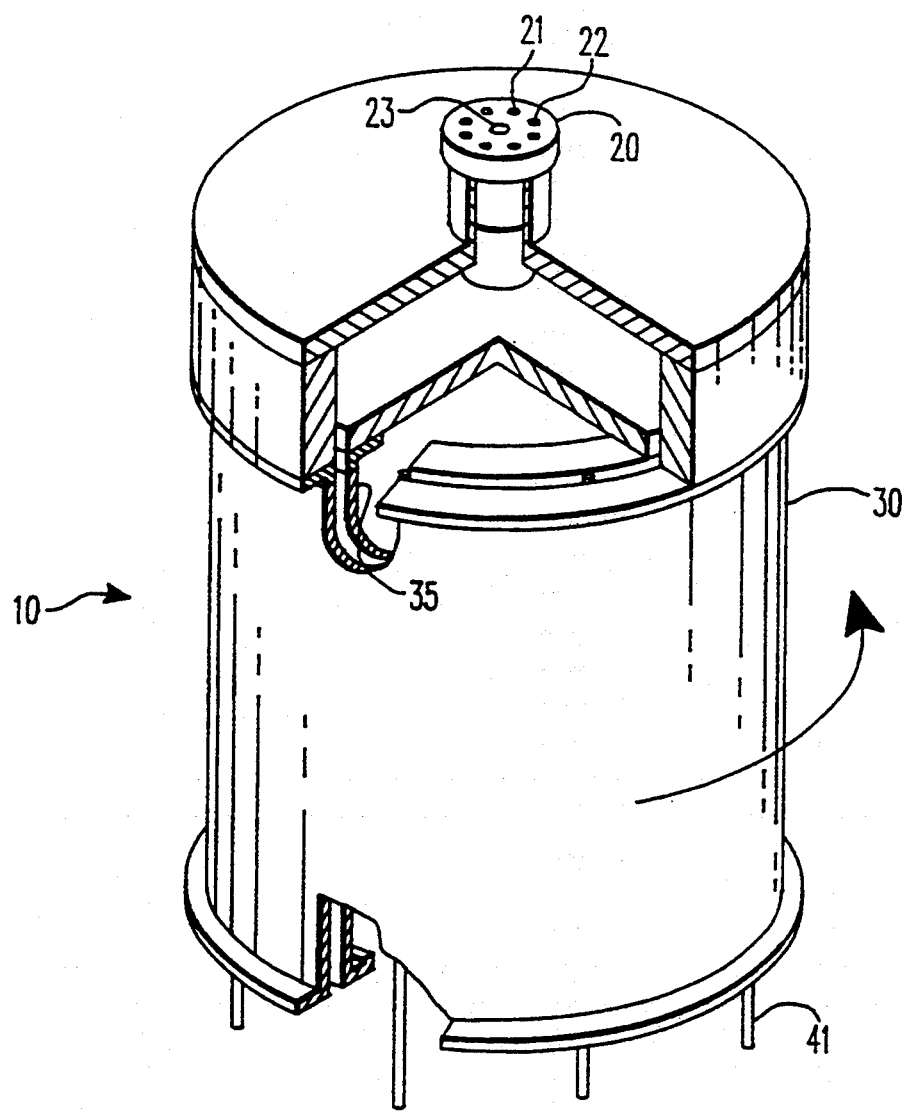
FIG. 1 is a perspective view of a continuous annular chromatograph (CAC) with a portion in section to illustrate the annular construction.
Figure 2:
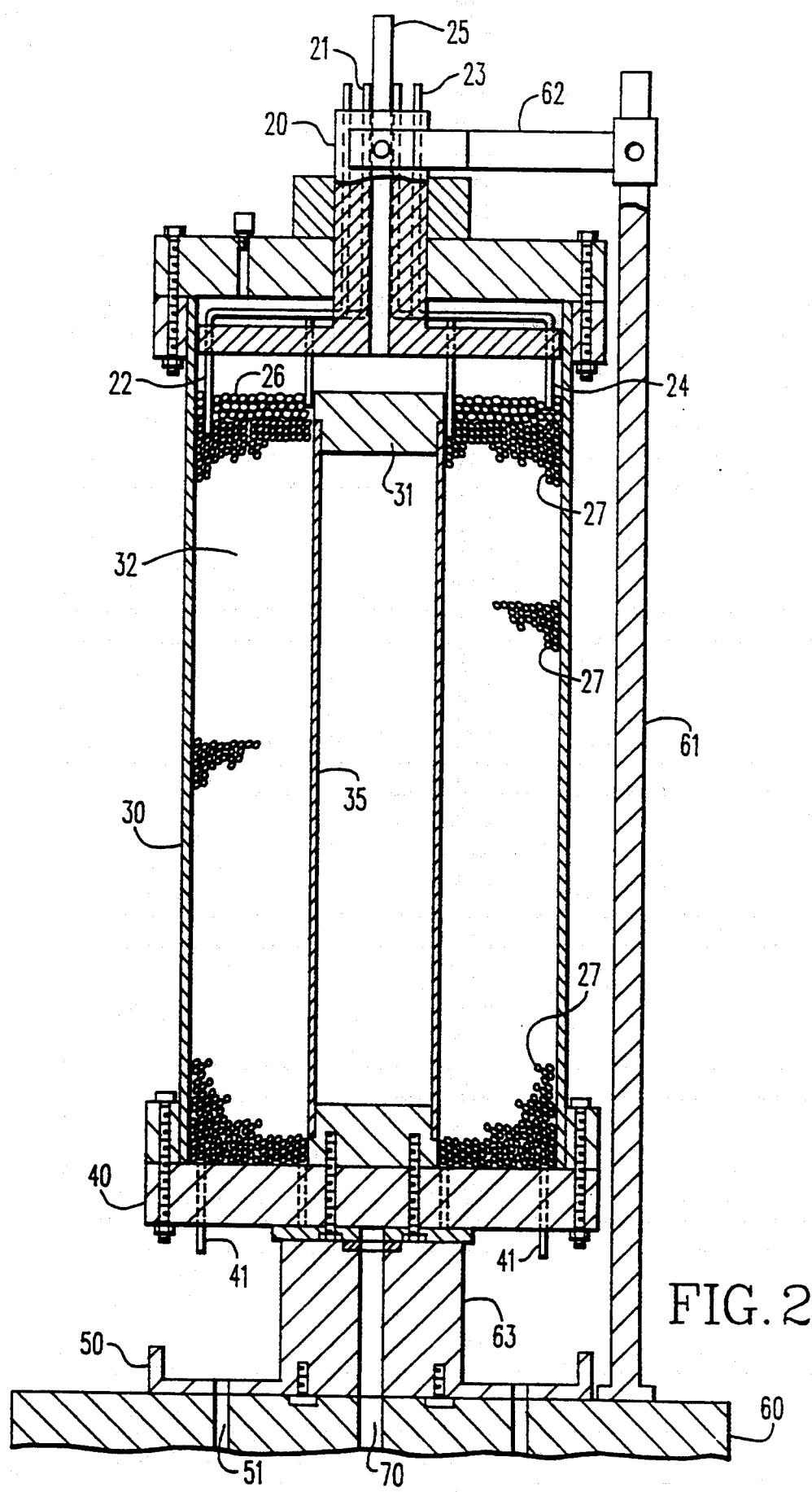
FIG. 2 is a longitudinal sectional view through the CAC of FIG. 1.
Figure 3:
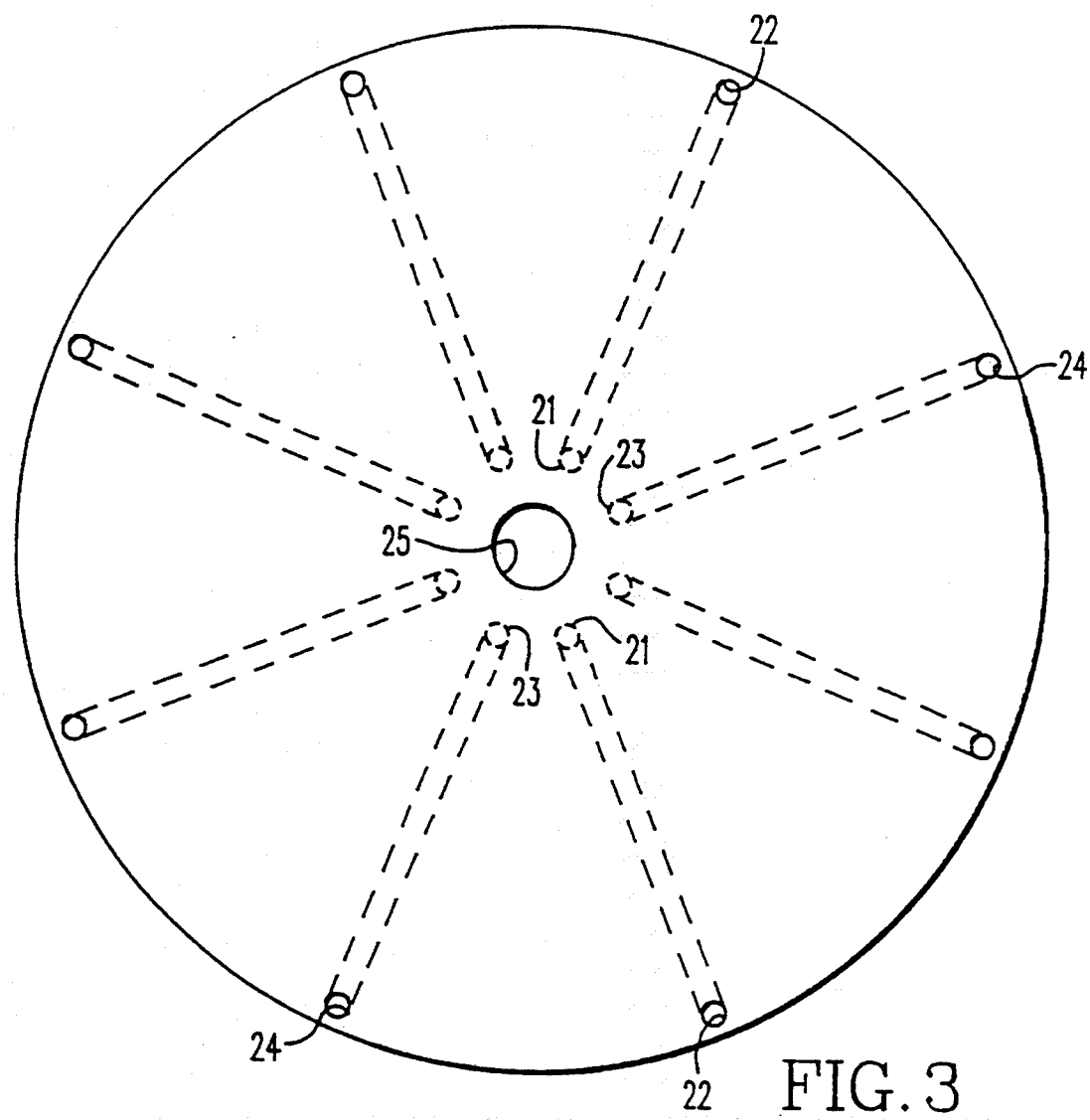
FIG. 3 is a plan view of the bottom of the item shown in FIG. 3.

The process according to the present invention effects the efficient and economical separation of high neutron capture cross-section erbium isotopes from mixtures containing erbium isotopes. Of particular interest is the continuous separation and isolation of the $^{167}$Er isotope.

The mixture that is treated according to the present invention can comprise a mixture of erbium isotopes that has previously been separated from other rare earth metals, or can also comprise a mixture of erbium isotopes and other rare earth metals, such as, for example, La, Ce, Pr, Nd, Sin, Eu, Tb, Dy, Ho, Gd, Tm, Yb, Lu, Y or the like. The separation of desired erbium isotopes is preferably effected by using a saturated cationic ion exchange resin which is the stationary phase, an aqueous solution of an ionic compound of a mixture of erbium isotopes which is the feed phase, and an aqueous acid eluant solution which is the mobile phase. Because of its ability to form anionic complexes in concentrated mineral acids (particularly acid halides), erbium enrichment may also be effected on anion exchange resin—as determined by the composition of the feed and mobile phases.

The starting material or feed phase used in the process according to the present invention can comprise a feed solution of a mixture of erbium oxides thereof that are converted to ions in solution, for example, by dissolving the mixture of erbium ions in nitric acid or other strong mineral acids, such as hydrochloric acid, sulfuric acid, butyric acid, or phosphoric acid or mixtures thereof. The feed phase is, therefore, any convenient solution of ionic erbium compounds formed from a mixture of erbium isotopes. The isotope mixture may be that which occurs in nature of it may be a partially refined mixture obtained from a preliminary refinement process.

In the embodiment using a cation exchange resin as the stationary phase, a preferred feed phase is that obtained from dissolving erbium in hydrochloride, which typically forms $Er^{+3}$ ions.

It is preferred that the feed phase have a concentration of erbium as high as possible without exceeding the solubility limit for the solute under the anticipated operating conditions. The natural consequence of chromatographic separation is a dilution of the concentration of the products being separated into product streams. Therefore, the overall efficiency of the process and particularly a minimization of the efforts needed to recover the desired products from the product streams is best served by using a high concentration as possible without creating an undue risk that erbium will precipitate out during the course of the process.

The stationary phase can be any cation exchange resin with an affinity for erbium cations-typically in aqueous solution as $Er^{3+}$ but which may also be complexed with $Cl^-$, $SO_4^{-2}$ or $PO_4^{-3}$ or other anions depending on the acid solvent. It is preferred that the cation exchange resin be capable of displaying a very strong affinity for such cations as reflected by a large solid-to-liquid distribution coefficient in dilute mineral acid solutions. It is particularly preferred that the "alpha" value of this coefficient be in excess of about 1.5 in acid solutions of less than about 7 Normal. It is particularly preferred to utilize cation exchange resins with the highest capacities possible-typically between about 0.1 and 1.0 milliequivalents per milliliter with a most probable capacity of about 0.1 to 0.5 milliequivalents per milliliter under elution conditions. Styrene-based sulfonic and carboxylic exchangers meet this requirement as do certain phenolic and carboxylic resins. When using anion exchanges, both weak and strong base resins are possible; quaternary, tertiary and porous strong base resins are preferred.

It is also preferred that the stationary phase comprise a monodisperse distribution of spherical particles with an average particle size of less than about 20 to 50 microns, more preferably less than about 10 microns. Decreasing particle diameter, however, offers the trade-off of improved separation for greater pressure drop. An especially preferred stationary phase is sulfonated cross linked polystyrene beads. But any moderate to strong acid resin will work for cation exchange or a strong base resin will work for anion exchange.

The feed phase may be any convenient solution of ionic erbium compounds formed from a mixture of erbium isotopes. The isotope mixture may be that which occurs in nature or it may be a partially refined mixture obtained from a preliminary refinement process.

A preferred feed phase is that obtained from hydrolyzing erbium oxide with hydrochloric acid. Crude erbium is commercially obtained from Molycorp in 98% purity or by dissolving/leaching the base rare-earth ores and separating the erbium fraction. The erbium fraction typically contains a natural distribution of isotopes and also contains impurity levels of other rare-earth elements (<2%). These compounds are readily hydrolyzed to yield an aqueous solution suitable for use in a chromatographic process. It is preferred to adjust the pH of this solution to the acidic range, particularly to between about 2N and 4N to reduce the chemical shock to the stationary phase in elution with a highly acidic eluant.

It is preferred that the feed phase be as concentrated as possible without exceeding the solubility limit for the solute. In the preferred feed phase, the solubility limit is about 4 g/100 g solution at 0° C. The *Handbook of Chemistry and Physics* lists both $ErCl_3$ and $Er(NO_3)_3$ as soluble.

The mobile phase may be an aqueous acid solution capable of solvating the erbium ions such that they can be eluted down the column. This mobile phase or eluant is a fluid capable of displacing the erbium ions from their ionic association with the stationary phase. It is preferably an aqueous solution of a strong mineral acid. Particularly preferred are sulfuric, hydrochloric (other aqueous acidic halides) and nitric acid, with nitric and hydrochloric acid being especially preferred and noting that either cation or anion exchange may work depending on solution concentrations. The acid strength needed is dependent on the identity of particular acid utilized but acid strengths of about 1.0 to 2.0 Normal or greater are preferred. An especially preferred eluant is between about 1.5 and 7.0 Normal and more preferably between about 1.5 and 4.0 Normal aqueous solutions, particularly when the mobile phase contains chloride ions.

The effective column height should be sufficient to allow significant resolution of the various isotopes of erbium into distinct product fractions. The resolution is preferably sufficient to yield an isotope purity in excess of about 50 percent, more preferably at least about 80 percent. It is preferred that this resolution be effected in a single pass through the column, since any removal and reinjection to a second column can result in back mixing and loss of some separation within various product fractions. The effective column height needed for a given resolution can be estimated from an application of the Kremser-Brown-Saunders equation, to empirical data on the separation capacity of a given stationary phase, mobile phase, eluent and flow conditions.

A separation factor, $\alpha$, is used to define this separation capacity. This factor is itself defined by the following formula for the binary case:

$$\alpha = \frac{y/(1-y)}{x/(1-x)}$$

wherein y is the mole fraction of the desired isotope in the product faction rich in that isotope and x is the mole fraction of this same isotope in the tails fraction. Approximate calculations can be performed by selecting one isotopic fraction as the product, and defining the tails fraction as the composite of the other product fractions. Thus, if a product fraction is obtained in which 80% of the erbium is erbium 167 and if in the composite of all the other isotopes together is only 20% of the erbium, the $\alpha$ defining this separation would be as follows. Calculation of separation factor, $\alpha$ $\alpha$ depends on purity of heads, and on the amount of the product isotope that is isolated in the heads fraction, i.e. the cut.

For heads purity of 80% with recovery of 80% of the erbium 167, the necessary $\alpha$ is $y = .8$ $x = \frac{.2 \times .2294}{.8 \times (1 - .2294) + .2 \times .2294}$ $0.2294$ = mole fraction of $^{167}$Er in natural Er.

$$\alpha: = \frac{\frac{y}{(1-y)}}{\left(\frac{x}{1-x}\right)}$$

$x = 0.069$
$y = 0.8$
$\alpha = 53.747$

Note that for a given degree of separation, at least if the individual isotope elution bands partially overlap, there is a tradeoff between purity and cut. By taking a smaller cut, the purity of the product may be increased.

Bench scale, multi-stage separation factors, $\alpha_s$, for isotopic separations are conveniently evaluated on 25 to 100 cm columns with 100 cm length being preferred. For such columns $\alpha$ values for erbium 167 on the preferred stationary phase with the preferred eluant are greater than about 1.001, preferably greater than about 1.005.

The effective column length N required for any desired degree of purification is then determined from this data. For instance, if a 25 cm test volume yields a separation factor, $\alpha$, of 1.085, this can be used as the separation factor for a theoretical stage, $\alpha_s$, in applying the Kremser-Brown-Saunders equation in estimating the number of theoretical stages. For the case being discussed, this yields the following result:

$$N = \frac{\left[\ln\frac{Y_{NP+1} - mX_0}{Y_1 - mX_0}\left(1 - \frac{1}{A}\right) + \frac{1}{A}\right]}{\ln A}$$

NP+1 = product stage
0 = feed stage
A = adsorption factor
m = slope of equilibrium curve Normal values for x, y, m and A result in required column lengths of 80 meters to 200 meters. The following table shows projected column length as a function of $\alpha$ and desired product purity. It is based on the assumption that the Kremser-Brown Saunders equation holds in the Underwood-Fenske form assuming the binary mixture approximation:

| $\alpha$ for 0.25 M Test Column | 98% Purity | | 95% Purity | |
|---|---|---|---|---|
| | No. of Stages | Total Col. Length (M) | No. of Stages | Total Col. Length (M) |
| 1.001 | 7830 | 1960 | 4970 | 1744 |
| 1.01 | 786 | 200 | 500 | 175 |
| 1.03 | 265 | 66 | 168 | 42 |
| 1.09 | 102 | 26 | 65 | 16 |
| 1.1 | 82 | 21 | 52 | 13 |

The effective column height can be vertical but it may have other orientations. What is important is the effective path over which the mobile phase travels.

It is preferred that the path be provided in such a way that the chromatographic separation can be operated continuously. There is no convenient technique currently available for instantaneously sensing the concentration of any given isotope of erbium. Thus, there is a preference for a continuously operating procedure which has reached steady state so that a particular product fraction reproducibly has a certain isotope distribution. If the chromatographic separation is effected in a discontinuous or batch manner, random variations between runs may make it difficult to reproducibly collect product fractions with the same isotope distributions from run to run. For instance, if a single vertical column is loaded in a batch manner, the elution time of the product fraction rich in a particular isotope may vary from run to run due to random variables difficult to control such as feed concentration fluctuations, etc.

A particularly preferred continuously operating chromatograph is the continuous annular chromatograph. This device was developed by Oak Ridge National Laboratory and comprises an annular stationary phase which is rotated about the axis of the annulus. U.S. Pat. No. 5,098,678 is incorporated by reference. The annulus is provided by packing the stationary phase material, such as resin beads, between two concentric cylinders of differing diameters with vertical axes. A feed port is provided at a given angular position and one or more eluant ports are provided at some angular offset from the feed port. It is preferred to place a layer of glass beads above the stationary phase and to feed the eluant to the glass beads while feeding the erbium feedstock directly to the top of the stationary phase. This should prevent any undesired mixing effects.

This device is provided with a number of product ports set at a number of angular positions which can be set arbitrarily to accommodate a particular set of operating conditions. Each product port collects an elution volume which has had a particular residence time on the column. The stationary phase is typically rotated at a constant speed so that any vertical segment of the annular bed is above a particular fixed product collection port at a given time after this segment has been loaded with erbium feedstock and eluant. Thus, each product collection port has an angular position which corresponds to a particular elution time for a particular rate of rotation of the stationary phase and for a particular flow rate through the stationary phase.

The flow rate through the stationary phase is controlled by the pressure drop across the effective height of the stationary phase and the physical characteristics of the stationary phase, i.e., particle size and packing void volume. This pressure drop may be provided by the hydrostatic head of the feedstock and eluant but it is preferably provided by pressurizing the device. The pressure required to achieve a particular flow rate is governed by the nature of the stationary phase; the smaller the average particle of the resin beads making up the stationary phase the larger the pressure drop required to obtain a particular flow rate over a particular effective height. However, the separation factor for any given theoretical stage is improved as the average particle size of the resin beads is decreased. Thus, the effective height needed to effect a given degree of separation is decreased as the separation capacity of a unit length (or theoretical stage height) is increased by decreasing the average particle size of the resin beads.

The flow rate across the effective height of the stationary phase and the rotational speed of the stationary phase should be coordinated such that a particular product fraction always eludes at the same angular position and thus is always delivered to the same product collection port.

It is preferred that the chromatograph be operated in a displacement mode wherein no more than about 5 percent, more preferably no more than about 1 percent of the effective column height, is loaded with feed solution before elution is initiated. This is conveniently effected by using a feed solution which has insufficient acid strength to release the erbium cations from ionic bonding with the cation exchange resin and loading no more than about 5 percent, preferably about 1 percent (or less) of the effective height, before adding an eluent of sufficient strength to cause the erbium cations to migrate down the column at a reasonable rate. In the continuous annular chromatograph this end is achieved by coordinating the angular displacement between the feed port and the eluant port and the speed of rotation of the annular bed so that the time interval between loading and elution is just sufficient for the desired degree of penetration. The relationship between the time for loading and the depth of penetration is in turn governed by the flow rate through the annular bed.

The displacement may be effected by either an isocratic or a gradient supply of eluant. In the former case, the eluant can simply be supplied from a single port while in the latter case, several ports at successively greater angular displacements from the feed port are utilized. In the gradient mode, elution under the influence of the initial eluant is permitted to proceed until some separation of the erbium isotopes has been effected and then a higher acid strength eluant is supplied. This increases the migration speed of the erbium cations down the column and minimizes the range of elution volumes or times over which a given component or product fraction will exit the column or, in other words, this procedure minimizes the band spreading.

Decreasing the elution volumes by gradient elution or by other means increases the concentration of the product i.e., the erbium isotope, in the product fraction. Product fraction concentrations greater than about 1.5 g/l, especially between about 5 and 20 g/l are preferred.

The flow rate down the column is governed by the pressure drop from the top to the bottom of the column and the nature of the stationary phase. The smaller the average particle size of the resin beads making up the stationary phase, the higher the pressure drop required to obtain a given flow rate. This relationship is also effected by the particle size distribution of these resin beads. There is, however, a maximum attainable flow rate for any given cation exchange resin stationary phase which cannot be exceeded by the application of additional pressure. The suppliers of such resins rate them in terms of flow rate per given pressure drop and maximum attainable flow rate.

It is preferred to use a stationary phase which will permit flow rates between about 0.1 and 20 gallons per minute per square foot of cross sectional area. There is a relationship between the achievable flow rates and the effective column height needed for a given degree of purity. For a given system of stationary phase and eluant, the theoretical stage separation factor, $\alpha_s$, of the stationary phase will increase as the average particle size of the resin beads of the stationary phase decreases. However, as this particle size decreases so does the flow capacity of the stationary phase. Thus, there is an inverse relationship between $\alpha_s$ and the flow capacity. Thus, a higher flow rate will require a greater effective column height to achieve the same degree of separation or product fraction purity.

Furthermore, there is the additional constraint that the pressure required to achieve the desired flow rate not exceed the capability of available pumps, seals and feed tubing. The required pressure is a function of both the pressure drop needed per unit of effective height and the total effective height required for the desired degree of separation. Thus, as the flow capacity of the stationary phase is increased by a change in its physical configuration and consequently its theoretical stage separation factor, $\alpha_s$, is decreased, the required effective height and the required overall pressure drop are both increased. On the other hand, as the theoretical stage separation factor, $\alpha_s$, is increased by a change in the resin bead size distribution and consequently the flow capacity of the stationary phase is decreased, the pressure drop for a given effective height is increased. A pressure drop of less than about 2758 kPa (400 psi), more especially between about 345 and 1042 k Pa (50 and 150 psi) is preferred.

Thus, to obtain a system with a commercially practical capacity, it is necessary to use a stationary phase which will simultaneously display both a reasonable theoretical stage factor, $\alpha_s$, and a reasonable flow rate per unit of effective height with a reasonable pressure drop. This can be achieved by an appropriate selection of both the ionic capacity of the stationary phase cation exchange resin and the eluant.

In a preferred mode, several product collection ports are used to collect a particular product fraction. This is accomplished by closely spacing these collection ports so that they more than span the angular range of rotation that corresponds to the elution time interval of that particular fraction but do not extend to angular positions at which any significant portion of any other product fraction is expected to elute. Of course, this requires that the elution time intervals of different product fractions do not substantially overlap. This arrangement tends to insure that minor fluctuations in the steady state elution behavior which would cause a slight advancement or retardation of the elution time of the desired product fraction will not result in any loss of this fraction.

The chromatograph may be configured to separate just the isotopes of erbium from a mixture of erbium isotopes or to also separate the isotopes of erbium from a mixture of erbium isotopes and other rare earth metals. In the latter case, all the other rare earth metals will be collected as a single product fraction although this may involve combining the output of a number of product ports. Of course, if the elemental separation is effected in one column and the isotopic separation or separations in another, the operating conditions in ,each column may be optimized with regard to the functions of that column.

A particular preferred device for use in practicing the present invention is illustrated in FIGS. 1 through 4. The continuous annular chromatograph 10 illustrated in FIG. 1 comprises two concentric cylinders 30 and 35 which define the annular space 32 seen in FIG. 2. Atop this annular space 32 is a distributor plate 20. Feed pipes or channels 21 and 23 run through the distributor plate 20 and terminate in feed nozzles 22 and 24, respectively. The feed nozzles 22 are intended to supply the feed phase to the exchange resin beads 27 which are packed in the annular space 32. For ease of illustration, these beads are shown as only partially filling the annular space 32. On the other hand, the feed nozzles 24 are intended to feed the eluant to the layer of glass beads 26 which sits atop the exchange resin beads 27. Thus the feed nozzles 24 are somewhat shorter than the feed nozzles 22. This feed arrangement serves to avoid any back mixing of the feed phase.

The central cavity defined by the inner cylinder 35 is sealed by a cap 31 so that pipe or channel 25 can be used to apply pressure to the annular bed of resin beads 27.

Figure 4:
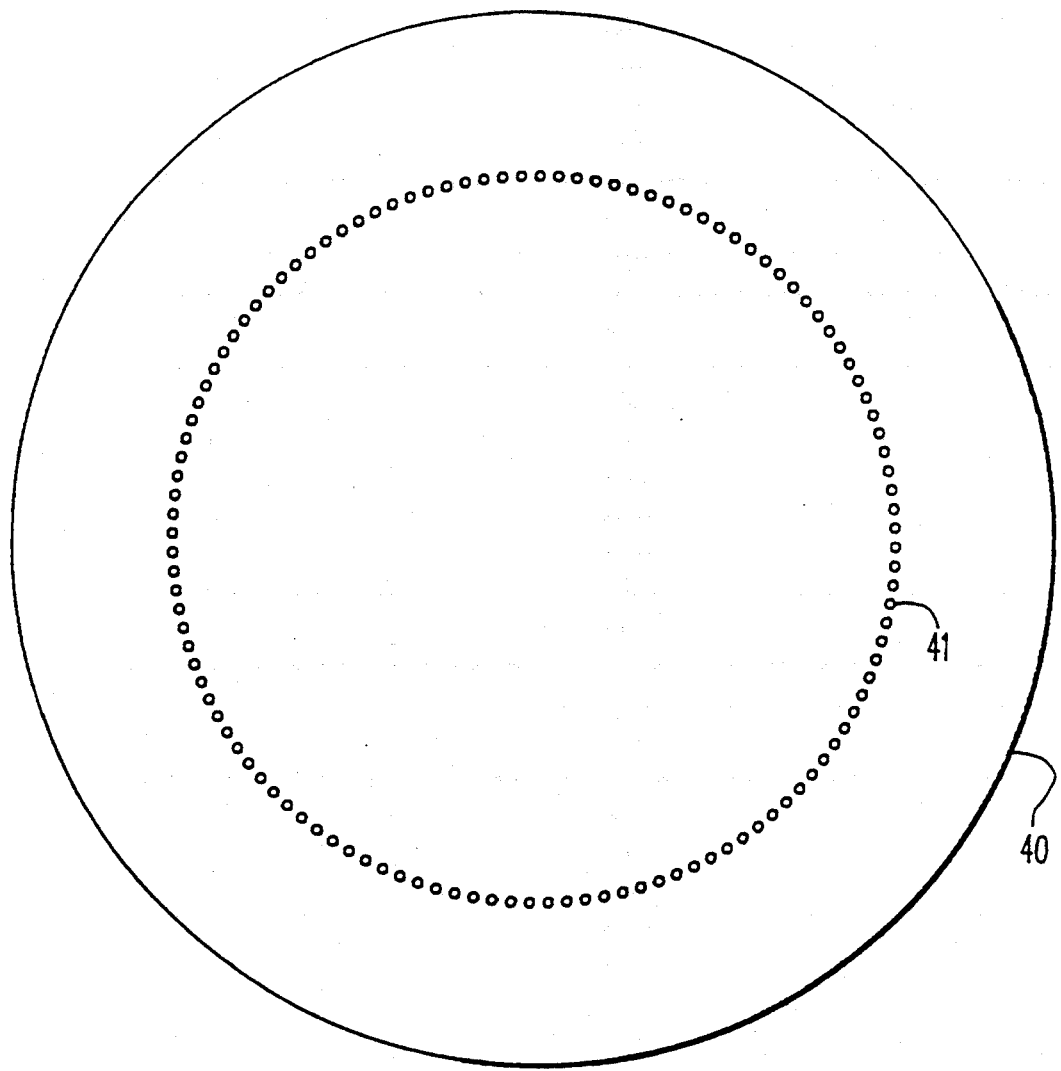
FIG. 4 is a plan view of the bottom of the CAC.

The bottom of the annular space 32 is defined by a product plate 40. As seen in FIG. 4, a large number of product delivery channels or pipes 41 pass through this plate. This allows the collection of a variety of product fractions and also facilitates adjustments to the operating conditions to allow product collection at various angular displacements.

The distributor plate 20 is held in a fixed position above the annular space 32 by a bracket 62 which is turn connected to a support rod 61 which is affixed to a base plate 60. Also affixed to this base plate 60 is a support column 63 on which the product plate 40 rotatably rests. A shaft 70 passes through this support column 63 and base plate 60 and connects the product plate 40 to a motivating means not shown. Also affixed to the base plate 60 is an annular collection trough 50 which can be subdivided into any number of convenient segments, each with its own exit port 51.

The continuous annular chromatograph 10 is operated by rotating the annular space 32 packed with the resin beads 27 beneath the fixed distributor plate 20 and its associated feed nozzles 22 and 24. The rotational force is supplied by the shaft 70.

The erbium isotopes are sequentially stripped from the ion exchange resin and form the fraction of desired isotopes as a downwardly moving band of eluant solution containing the same. The desired fraction, when it reaches the desired product port of the column, may be readily collected and separated from the remainder of the eluant solution. The isolation of the desired erbium isotope is accomplished by obtaining the proper separation factor and isolating the desired erbium isotope 167 based on the proper exit time in the proper ports.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims.

We claim:

1. A continuous chromatographic process for the simultaneous separation of each isotope of erbium in a sample containing a mixture of erbium isotopes to produce substantially pure fractions of each separated isotope, wherein said process includes the steps of:
   (a) loading a chromatographic separation column having an effective length sufficient to resolve each said erbium isotope into a distinct product fraction having a purity greater than about 50% with a cation exchange resin having an affinity for erbium cations; said resin having a solid to liquid separation factor in excess of about 1.02 in acid solutions of less than about 7–8 Normal;
   (b) preparing an aqueous feed solution of ionic erbium from said sample having a pH of between about 0 and 5 and a solubility limit of about 40 g/l;
   (c) preparing an eluant capable of displacing erbium ions from said exchange resin, wherein said eluant is an aqueous solution of a strong mineral acid having a normality greater than about 1N;
   (d) feeding said aqueous erbium feed solution to the top of said loaded chromatographic separation column so that said feed solution begins to travel down said column;
   (e) feeding said mineral acid eluant to the top of said column to cause each of the erbium isotopes in said feed solution to pass downwardly through said column at a different speed; and
   (f) collecting a separate erbium isotope containing product fraction having an isotope purity greater than 50% at the bottom of said column for at least one of the isotopes present in said sample.

2. The process of claim 1, wherein the product fraction of said isotope has an isotope purity of at least about 80%.

3. The process described in claim 1, wherein said at least one isotope is erbium 167.

4. The process described in claim 1, wherein the cation exchange resin is a monodisperse distribution of spherical beads having an average particle size of about 20–50 microns or less and has an exchange capacity of between 0.1 and 0.5 milliequivalents for erbium cations.

5. The process described in claim 1, wherein the separation factor of said column for a theoretical stage having a height of 25 cm for erbium 167 is at least about 1.03.

6. The process described is claim 1, wherein said erbium isotope-containing sample is separated from said erbium isotope during said continuous chromatographic process using organic acids that form complexes with the Er$^{+3}$ ions and collected as a separate fraction in steps (e) and (f).

7. The process of claim 6, wherein the organic acid is citric acid.

8. The process described in claim 1, wherein said chromatographic separation column is located in a circumferential annular space of a continuous annular chromatograph.

9. A continuous steady state chromatographic process for producing commercially useful quantities of the erbium 167 isotope including the steps of:
(a) preparing an acidic aqueous feed solution of an erbium compound containing said erbium isotopes having a pH between about 0 and 5;
(b) preparing a stationary phase comprising a cation exchange resin with a monodisperse particle distribution of substantially spherical particles having an average particle size less than or equal to about 50 microns; a capacity for erbium cations of between about 0.1 and 1.0 meg/mi.; and a separation factor for erbium 167 for a 1.03-1.05 cm theoretical stage of at least about 25 cm;
(c) rotating said chromatograph;
(d) loading said stationary phase into a circumferential annular space of a continuous annular chromatograph so that the stationary phase has an effective height sufficient to yield a erbium 167 production fraction comprising 5-15 g/l tool percent erbium 167;
(e) while said chromatograph is rotating feeding said erbium isotope-containing feed solution to the top of the continuous annular chromatograph so that feed solution penetrates about 5% of the effective height of the stationary phase;
(f) feeding a continuous supply of an acid eluant having a normality between about 1.0 and 7 into the top of the annular stationary phase to at least one circumferential location;
(g) while the continuous annular chromatograph is rotating, continuing to feed said erbium isotope-containing feed solution and said eluant into the annular stationary phase to cause said feed solution and said eluant to flow downwardly to the bottom of the chromatograph;
(h) after all of the erbium isotopes have been eluted, collecting a separate production fraction at the bottom of the chromatograph corresponding to the low thermal neutron cross-section erbium isotope present in said aqueous feed;
(i) continuously carrying out steps (d) through (g) to produce said commercially useful quantities of said low thermal neutron cross-section erbium isotope.

10. The process described in claim 9, wherein said erbium isotope-containing compound is erbium citrate and said eluant is citric acid.

11. The process described in claim 9, wherein said eluant is fed into the top of the annular stationary phase at a plurality of circumferential locations and the concentration of said acid eluant is increased at each successive feed location moving in the direction of rotation of the continuous annular chromatograph.

12. The process described in claim 9, wherein said erbium isotope product fractions comprise erbium 167.

13. A continuous, steady-state chromatographic process for the simultaneous separation of each of the isotopes of erbium to produce substantially pure fractions of increased thermal neutron cross-sections without the use of hazardous organic solvents, comprising the steps of:
(a) subjecting a feed phase solution of erbium ions to continuous, steady-state, chromatography in a continuous annular chromatograph using a cation exchange resin as the stationary phase and an eluant solution as the mobile phase; and
(b) collecting continuously at least one erbium product fraction enriched in $^{167}$Er to yield erbium having increased thermal neutron cross-sections.

* * * * *